US00PP24340P2

(12) United States Plant Patent
Eveleens

(10) Patent No.: US PP24,340 P2
(45) Date of Patent: Mar. 25, 2014

(54) CARNATION PLANT NAMED 'HILBREYE'

(50) Latin Name: *Dianthus caryophyllus*
Varietal Denomination: Hilbreye

(75) Inventor: Peter Eveleens, Aalsmeer (NL)

(73) Assignee: Hilverda Kooij B.V., De Kwakel (NL)

( * ) Notice: Subject to any disclaimer, the term of this patent is extended or adjusted under 35 U.S.C. 154(b) by 81 days.

(21) Appl. No.: 13/506,826

(22) Filed: May 17, 2012

(51) Int. Cl.
*A01H 5/00* (2006.01)

(52) U.S. Cl.
USPC ..... Plt./273

(58) Field of Classification Search
USPC ..... Plt./273
See application file for complete search history.

(56) References Cited

PUBLICATIONS

UPOV PLUTO 201303 QZ Citation for 'Hilbreye' Aug. 15, 2012.*

* cited by examiner

*Primary Examiner* — Wendy C Haas
(74) *Attorney, Agent, or Firm* — C. A. Whealy

(57) ABSTRACT

A new and distinct cultivar of Carnation plant named 'Hilbreye', characterized by its upright, somewhat outwardly spreading and uniformly mounded plant habit; freely branching habit; freely flowering habit; large white and purple bi-colored double flowers that are positioned above and beyond the foliar plane on strong peduncles; and good garden performance.

1 Drawing Sheet

Botanical designation: *Dianthus caryophyllus.*
Cultivar denomination: 'HILBREYE'.

BACKGROUND OF THE INVENTION

The present invention relates to a new and distinct cultivar of Carnation plant, botanically known as *Dianthus caryophyllus*, grown commercially as a potted and garden plant and hereinafter referred to by the name 'Hilbreye'.

The new Carnation plant is a product of a planned breeding program conducted by the Inventor in De Kwakel, The Netherlands. The objective of the breeding program is to create new potted Carnation plants that have uniform plant habit and numerous unique and attractive flowers.

The new Carnation plant originated from a cross-pollination made by the Inventor in De Kwakel, The Netherlands in May, 2008 of *Dianthus caryophyllus* 'Margarita', disclosed in U.S. Plant Pat. No. 17,335, as the female, or seed, parent with *Dianthus caryophyllus* 'Odessa Easy Pink', not patented, as the male, or pollen, parent. The new Carnation plant was discovered and selected by the Inventor as a single flowering plant from within the progeny of the stated cross-pollination in a controlled greenhouse environment in De Kwakel, The Netherlands in July, 2009.

Asexual reproduction of the new Carnation plant by terminal cuttings propagated in a controlled greenhouse environment in De Kwakel, The Netherlands since 2009 has shown that the unique features of this new Carnation plant are stable and reproduced true to type in successive generations of asexual reproduction.

SUMMARY OF THE INVENTION

Plants of the new Carnation have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilbreye'. These characteristics in combination distinguish 'Hilbreye' as a new and distinct Carnation plant:

1. Upright, somewhat outwardly spreading and uniformly mounded plant habit.
2. Freely branching habit.
3. Freely flowering habit.
4. Large white and purple bi-colored double flowers that are positioned above and beyond the foliar plane on strong peduncles.
5. Good garden performance.

Plants of the new Carnation differ from plants of the female parent, 'Margarita', in the following characteristics:

1. Plants of the new Carnation are more vigorous than plants of 'Margarita'.
2. Plants of the new Carnation have larger flowers with more petals per flower than plants of 'Margarita'.
3. Plants of the new Carnation have longer branches than plants of 'Margarita'.
4. Plants of the new Carnation and 'Margarita' differ in flower coloration.

Plants of the new Carnation differ from plants of the male parent, 'Odessa Easy Pink', in the following characteristics:

1. Plants of the new Carnation and 'Odessa Easy Pink' differ in leaf color.
2. Plants of the new Carnation have larger flowers than plants of 'Odessa Easy Pink'.
3. Plants of the new Carnation and 'Odessa Easy Pink' differ in flower color.

Plants of the new Carnation can be compared to plants of *Dianthus caryophyllus* 'Koes', disclosed in U.S. Plant Pat. No. 22,370. In side-by-side comparisons conducted in De Kwakel, The Netherlands, plants of the new Carnation differed from plants of 'Koes' in the following characteristics:

1. Plants of the new Carnation had larger flowers than plants of 'Koes'.
2. Plants of the new Carnation had longer branches than plants of 'Koes'.
3. Plants of the new Carnation and 'Koes' differed in flower color.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant. The photograph comprises a side perspective view of a typical flowering plant of 'Hilbreye' grown in a container.

DETAILED BOTANICAL DESCRIPTION

Plants used in the aforementioned photograph and following observations and measurements describe plants grown during the late winter and early spring in 12-cm containers in a glass-covered greenhouse in De Kwakel, The Netherlands and under cultural practices which approximate those generally used in commercial potted Carnation production. During the production of the plants, day and night temperatures averaged 12° C. and light levels averaged 7,000 lux. Plants were pinched one time five weeks after planting. Plants used for the description were 17 weeks old and plants used for the photograph were 25 weeks old. In the following description, color references are made to The Royal Horticultural Society Colour Chart, 2007 Edition, except where general terms of ordinary dictionary significance are used.

Botanical classification: *Dianthus caryophyllus* 'Hilbreye'.

Parentage:

*Female, or seed, parent.*—*Dianthus caryophyllus* 'Margarita', disclosed in U.S. Plant Pat. No. 17,335.

*Male, or pollen, parent.*—*Dianthus caryophyllus* 'Odessa Easy Pink', not patented.

Propagation:

*Type*.—By terminal cuttings.

*Time to initiate roots, summer*.—About six days at 20° C. to 25° C.

*Time to initiate roots, winter*.—About eight days at 18° C.

*Time to produce a rooted young plant, summer*.—About three weeks at 20° C. to 25° C.

*Time to produce a rooted young plant, winter*.—About five weeks at 18° C.

*Root description*.—Medium in thickness, fibrous; white in color.

*Rooting habit*.—Moderate branching; medium density.

Plant description:

*Plant type and form*.—Herbaceous perennial; upright, somewhat outwardly spreading and uniformly mounded plant habit; broad inverted triangle.

*Branching habit*.—Freely-branching growth habit; when pinched, about seven basal branches develop; dense and bushy growth habit.

*Plant height*.—About 16.5 cm.

*Plant diameter or spread*.—About 22.3 cm.

*Lateral branches*.—Length: About 9.8 cm. Diameter: About 3 mm. Internode length: About 2 cm. Strength: Strong. Texture: Smooth, glabrous. Color: Close to 137B.

Foliage description:

*Arrangement*.—Opposite, simple; sessile.

*Length*.—About 8.9 cm.

*Width*.—About 7 mm.

*Shape*.—Narrowly oblanceolate.

*Apex*.—Acute.

*Base*.—Attenuate, decurrent.

*Margin*.—Entire.

*Texture, upper and lower surfaces*.—Smooth, glabrous.

*Venation pattern*.—Parallel.

*Color*.—Developing leaves, upper and lower surfaces: Close to 143A; towards the base, close to 144D. Fully expanded leaves, upper surface: Close to N137C to N137D; venation, close to N137C to N137D. Fully expanded leaves, lower surface: Close to N137C; venation, close to 143A.

Flower description:

*Flower type and habit*.—Rotate double flowers usually arranged in terminal sprays; freely flowering habit with typically about 60 flowers developing per plant; flowers positioned above and beyond the foliar plane on strong peduncles; flowers face mostly upright.

*Fragrance*.—Flowers moderately fragrant; sweet, clove-like.

*Natural flowering season*.—Flowering is continuous through the summer and late summer in The Netherlands; plants begin flowering about 13 weeks after planting.

*Flower longevity*.—Flowers last about ten days on the plant; flowers not persistent.

*Spray height*.—About 8.3 cm.

*Spray diameter*.—About 9.7 cm.

*Flower diameter*.—About 5.7 cm.

*Flower depth*.—About 4.1 cm.

*Flower buds*.—Length: About 2.3 cm. Diameter: About 9 mm. Shape: Obovate. Color: Close to 137B.

*Petals and petaloids*.—Quantity and arrangement: About ten petals per flower arranged in the outer whorls and about ten petaloids (transformed stamens) per flower in the inner whorls. Length, petals: About 4.9 cm. Width, petals: About 2.9 cm. Length, petaloids: About 3.9 cm. Width, petaloids: About 1.5 cm. Shape, petals: Spatulate. Shape, petaloids: Irregularly narrow spatulate. Apex, petals and petaloids: Praemorse. Base, petals and petaloids: Acute. Margin, petals and petaloids: Entire. Texture, petals and petaloids, upper and lower surfaces: Smooth, glabrous; velvety. Color, petals and petaloids: When opening, upper surface: Towards the margin, close to 69D; central radial band, close to 187A; distal edge of band, close to N57B; proximal edge of band, close to N57D; towards the base, close to 144C. When opening, lower surface: Towards the margin, close to 69B to 69D; central radial band, close to 70B; distal and proximal edges of band, close to 70D; towards the base, close to 144C. Fully opened, upper surface: Towards the margin, close to NN155D; central radial band, close to 187B; distal edge of band, close to N57B; proximal edge of band, close to 63C; towards the base, close to 144C; color does not change with development. Fully opened, lower surface: Towards the margin, close to NN155D; central radial band, close to 70B; distal and proximal edges of band, close to 73D; towards the base, close to 144C.

*Sepals*.—Quantity and arrangement: Five in a single whorl; proximal 75% of the sepals are fused. Length: About 2.3 cm. Width: About 6 mm. Shape: Oblong. Apex: Broadly acute. Margin: Entire. Texture, upper and lower surfaces: Smooth, glabrous. Color: When opening and fully opened, upper surface: Close to 146C to 146D; margins, close to 144C. When opening and fully opened, lower surface: Close to 137B; margins, close to 144C.

*Peduncles*.—Length: About 3.7 cm. Diameter: About 3 mm. Strength: Strong. Aspect: Erect to about 35° from vertical. Texture: Smooth, glabrous. Color: Close to 137B.

*Reproductive organs*.—Stamens: None observed, all transformed into petaloids. Pistils: Quantity: About two per flower. Pistil length: About 3 cm. Stigma shape: Pointed; strongly curved. Stigma color: Close to N155B. Style length: About 2.6 cm. Style color: Close to NN155B. Ovary color: Close to N144A; towards the base, close to 150D.

*Fruits and seeds*.—Fruit and seed development have not been observed on plants of the new Carnation.

Disease & pest resistance: Plants of the new Carnation have not been observed to be resistant to pathogens and pests common to Carnation plants.

Garden performance: Plants of the new Carnation have been observed to have good garden performance and to tolerate wind, rain and temperatures ranging from about 5° C. to 35° C. and to be hardy to USDA Hardiness Zone 9.

It is claimed:

1. A new and distinct Carnation plant named 'Hilbreye' as illustrated and described.

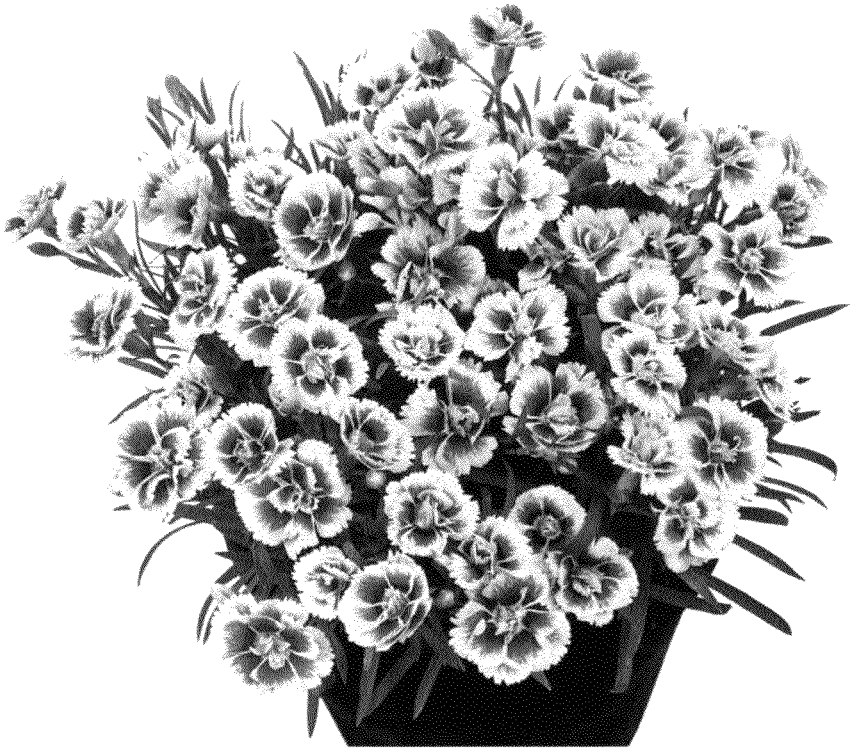

* * * * *